United States Patent
Morris et al.

(10) Patent No.: US 10,816,610 B2
(45) Date of Patent: Oct. 27, 2020

(54) APPARATUS AND METHOD FOR IDENTIFYING DEFECTIVE CABLES

(71) Applicant: Genii, Inc., St. Paul, MN (US)

(72) Inventors: Marcia L. Morris, St. Paul, MN (US); Jose Doval, St. Paul, MN (US); Patrick Kehl, St. Paul, MN (US)

(73) Assignee: Genii, Inc., St. Paul, MN (US)

( * ) Notice: Subject to any disclaimer, the term of this patent is extended or adjusted under 35 U.S.C. 154(b) by 14 days.

(21) Appl. No.: 15/711,449

(22) Filed: Sep. 21, 2017

(65) Prior Publication Data

US 2018/0080969 A1    Mar. 22, 2018

Related U.S. Application Data

(60) Provisional application No. 62/397,789, filed on Sep. 21, 2016.

(51) Int. Cl.
*G01R 31/58* (2020.01)
*G01R 31/44* (2020.01)
(Continued)

(52) U.S. Cl.
CPC .......... *G01R 31/58* (2020.01); *A61B 18/1233* (2013.01); *G01R 31/44* (2013.01);
(Continued)

(58) Field of Classification Search
CPC .......... G01R 31/021–023; G01R 31/44; G01R 31/1272; G01R 31/045; G01R 31/08;
(Continued)

(56) References Cited

U.S. PATENT DOCUMENTS

| 5,155,440 A * | 10/1992 | Huang | G01R 31/58 324/539 |
| 6,680,728 B1 * | 1/2004 | Lilenfeld | G06F 3/0338 345/156 |

(Continued)

OTHER PUBLICATIONS

Keysight Technologies. FieldFox Handheld Analyzers. pp. 1-66; Copyright 2014. (Year: 2014).*

(Continued)

*Primary Examiner* — Patrick Assouad
*Assistant Examiner* — Sean Curtis
(74) *Attorney, Agent, or Firm* — Viksnins Harris Padys Malen LLP

(57) ABSTRACT

In some embodiments, an apparatus includes a substrate having a smoothly bending surface to fit into a human hand. The substrate includes a start test switch, a first connector to couple to a first end of a cable, and a second connector to couple to a second end of the cable. The cable has an impedance. The electronic circuit is coupled to the, first connector and the second connector. In operation, the electronic circuit provides a first signal when the first end of the cable is coupled to the first connector and the second end is coupled to the second connector, the start switch is activated, and the impedance is between a minimum impedance value and a maximum impedance value. The electronic circuit provides a second signal when the first end of the cable is coupled to the first connector and the second end is coupled to the second connector, the start switch is activated, and the impedance is greater than the maximum impedance value.

13 Claims, 13 Drawing Sheets

(51) Int. Cl.
  *A61B 18/12* (2006.01)
  *A61B 18/00* (2006.01)
  *A61B 18/14* (2006.01)

(52) U.S. Cl.
  CPC ..... *A61B 18/14* (2013.01); *A61B 2018/00172* (2013.01); *A61B 2018/00875* (2013.01)

(58) Field of Classification Search
  CPC ... G01R 31/083; A61B 18/1233; A61B 18/14; A61B 2018/00172; A61B 2018/00875
  USPC ................................................. 324/539–544
  See application file for complete search history.

(56) References Cited

U.S. PATENT DOCUMENTS

| | | | | |
|---|---|---|---|---|
| 7,271,576 | B1* | 9/2007 | O'Harra, II | G01R 27/04 324/73.1 |
| 8,359,179 | B2* | 1/2013 | Bruce | A61B 5/0534 433/27 |
| 9,237,317 | B2* | 1/2016 | Hollinger | H04N 5/2252 |
| 9,341,357 | B2* | 5/2016 | Hollinger | H04N 5/2256 |
| 9,423,444 | B2* | 8/2016 | Dulger | G01R 31/54 |
| 9,625,508 | B2* | 4/2017 | Chayat | G01R 27/32 |
| 9,989,576 | B2* | 6/2018 | Vangool | H02H 3/165 |
| 10,203,361 | B2* | 2/2019 | Ugawa | G01R 27/00 |
| 2003/0141875 | A1* | 7/2003 | Seymour | G01R 31/67 324/525 |
| 2009/0033630 | A1* | 2/2009 | Thelen | H04N 21/42222 345/173 |
| 2009/0313767 | A1* | 12/2009 | Tanner | D06F 73/00 8/149.3 |
| 2011/0199107 | A1* | 8/2011 | Adamian | G01R 27/32 324/750.02 |
| 2013/0250047 | A1* | 9/2013 | Hollinger | H04N 7/183 348/36 |
| 2015/0028884 | A1* | 1/2015 | Dulger | G01R 31/58 324/538 |
| 2015/0159846 | A1* | 6/2015 | Hollinger | H04N 5/23206 362/183 |
| 2015/0212129 | A1* | 7/2015 | Chayat | H01P 5/028 324/638 |
| 2016/0084902 | A1* | 3/2016 | Westbrook | G01R 31/50 702/122 |
| 2016/0100035 | A1* | 4/2016 | Martis | H04L 67/34 709/203 |
| 2016/0231642 | A1* | 8/2016 | Hollinger | F21V 23/009 |
| 2017/0254871 | A1* | 9/2017 | Sestok, IV | G01R 27/14 |
| 2017/0257262 | A1* | 9/2017 | Dalal | H04L 43/50 |
| 2018/0080969 | A1* | 3/2018 | Morris | G01R 31/44 |
| 2020/0000348 | A1* | 1/2020 | Bartosch | A61B 5/02055 |

OTHER PUBLICATIONS

Keysight Technologies. Techniques for Advanced Cable Testing Using FieldFox handheld analyzers. Copyright 2015 (Year: 2015).*
Tech Nation. BioMed101: 10 best practices for electrosurgical testing. Jan. 2016. (Year: 2016).*
Wayback Archive Date of "Keysight—FieldFox HandHeld Analyzers" to Sep. 3, 2014. (Year: 2019).*

* cited by examiner

APPARATUS AND METHOD FOR IDENTIFYING DEFECTIVE CABLES

PRIORITY

This application claims priority to U.S. Provisional Application No. 62/397,789, which was filed Sep. 21, 2016. The entire content of the application referenced above is hereby incorporated by reference herein.

FIELD

The present disclosure is directed to an apparatus and methods for identifying defective cables.

BACKGROUND

Cables, such as high frequency electrosurgical cables, are used to deliver electrical current between high frequency current generators and applicators that provide medical treatments to patients. If the cables do not operate as intended, the only indication to the end user is an absence of thermal effect. This treatment delay can result in patient harm, delays in treatment time or other, sometimes serious, complications. This problem has existed for decades without solution. For these and other reasons, there is a need for the apparatus and methods of the present disclosure.

SUMMARY

In some embodiments, an apparatus includes a substrate having a smoothly bending surface to fit into a human hand. The substrate includes a start test switch, a first connector to couple to a first end of a cable, and a second connector to couple to a second end of the cable. The cable has an impedance. The electronic circuit is coupled to the first connector and the second connector. In operation, the electronic circuit provides a first signal when the first end of the cable is coupled to the first connector and the second end is coupled to the second connector, the start switch is activated, and the impedance is between a minimum impedance value and a maximum impedance value. The electronic circuit provides a second signal when the first end of the cable is coupled to the first connector and the second end is coupled to the second connector, the start switch is activated, and the impedance is greater than the maximum impedance value.

In some embodiments, a method includes holding in a human hand an apparatus for identifying characteristics of a high frequency electrosurgical cable having a first end, a second end, and an impedance, the apparatus including a first connector and a second connector, inserting the first end into a first connector and inserting the second end into the second connector, activating a start test switch of the apparatus to begin a test of the electrosurgical cable, and activating a first signal if the resistance is between a minimum impedance value and a maximum impedance value and activating a second signal if the impedance is greater than the maximum impedance value.

DESCRIPTION

Figure 1:
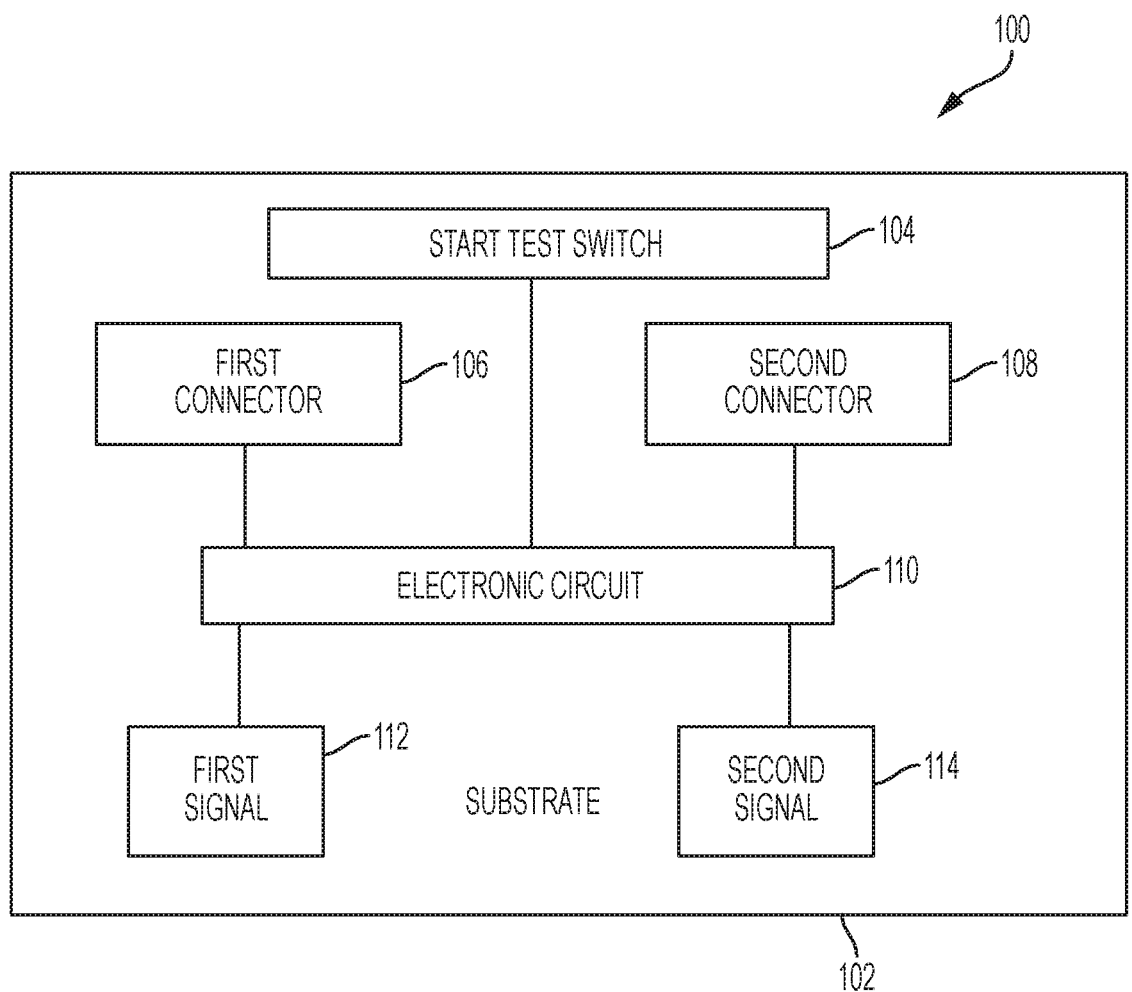
FIG. 1 shows a block diagram of an apparatus including a substrate, a start switch, a first connector, a second connector, and an electronic circuit, according to some embodiments of the present disclosure.

FIG. 1 shows a block diagram of an apparatus 100 including a substrate 102, a start switch 104, a first connector 106, a second connector 108, and an electronic circuit 110, according to some embodiments of the present disclosure. The substrate 102 has a smoothly bending surface (see FIG. 4) to fit into a human hand (see FIG. 4). The electronic circuit 110 is coupled to the first connector 106, the second connector 108 and the switch 104. In operation, the electronic circuit generates a first signal 112 and a second signal 114.

The substrate 102 provides an enclosure for the electronic circuit 110. An injection molding process may be used to form the substrate 102. The substrate 102 is not limited to being formed from a particular material. One exemplary material suitable for use in fabricating the substrate 102 is acrylonitrile butadiene styrene. In some embodiments, the finish of the substrate 102 is a matte finish. A matte finish is a dull, no-gloss finish without luster.

Closing the start switch 104 activates the electronic circuit 110 and initiates the testing of a cable coupled to the first connector 106 and the second connector 108. The start switch 104 is not limited to a particular type of switch. In some embodiments, the start switch 104 is a touch activated switch, such as a push-button switch, that is closed when depressed and open when released.

The first connector 106 and the second connector 108 are designed to receive and electrically couple to the first end and the second end of the cable being tested. In some embodiments, the first connector 106 is a high frequency electrosurgical cable connector. For example, for a high frequency electrosurgical cable, the first connector 106 is designed to electrically couple to the first end of the high frequency electrosurgical cable and the connector 108 is designed to electrically couple to the second end of the high frequency electrosurgical cable. In some embodiments, the first connector 106 couples to the first cable end having a first diameter and couples to the first cable end having a second diameter not equal to the first diameter. Thus, the first connector 106 is capable of coupling to at least two different cable ends having different diameters.

The electronic circuit 110 is designed to produce the first signal 112 when the impedance of the cable under test is within a specified range and the second signal 114 when the impedance of the cable under test exceeds the maximum value of the specified range. For example, in some embodiments, the electronic circuit 110 generates the first signal 112 when the impedance of the cable is between a minimum impedance value of about zero ohms and a maximum impedance value of about 1.1 ohms. And in some embodiments, the electronic circuit 110 generates the first signal 112 when the impedance of the cable is between a minimum impedance value of about 0.01 ohms and a maximum impedance value of about eight ohms.

The first signal 112 indicates that the impedance of the cable being tested is within the specified range. The second signal 114 indicates that the impedance of the cable being tested exceeds the specified range. In some embodiments, the first signal 112 and the second signal 114 are visual signals. In some embodiments, the first signal 112 is detectable by a human visual system. For example, in some embodiments the first signal 112 is provided by a substantially green light emitting diode or a light emitting device adapted to display a green signal and the second signal 114 is provided by a red light emitting diode or a light emitting device adapted to display a red signal. In some embodiments, the first signal 112 and the second signal 114 are auditory signals. In some embodiments, the first signal 112 is detectable by a human auditory system. For example, in some embodiments, the first signal 112 is a voice signal indicating that the impedance of the cable being tested is within the specified range and the second signal 114 is a voice signal indicating that the impedance of the cable being tested is not within the specified range.

In operation, the cable being tested (see FIG. 8) has a first end 802 a second end 804, and an impedance. The electronic circuit 110 provides the first signal 112 when the first end 802 of the cable is coupled to the first connector 106 and the second end 804 is coupled to the second connector 108, the start switch 104 is activated, and the impedance is between a minimum impedance value and a maximum impedance value. The electronic circuit 110 provides the second signal 114 when the first end 802 of the cable is coupled to the first connector 106 and the second end 804 is coupled to the second connector 108, the start switch 110 is activated, and the impedance is greater than the maximum impedance value.

Figure 2:
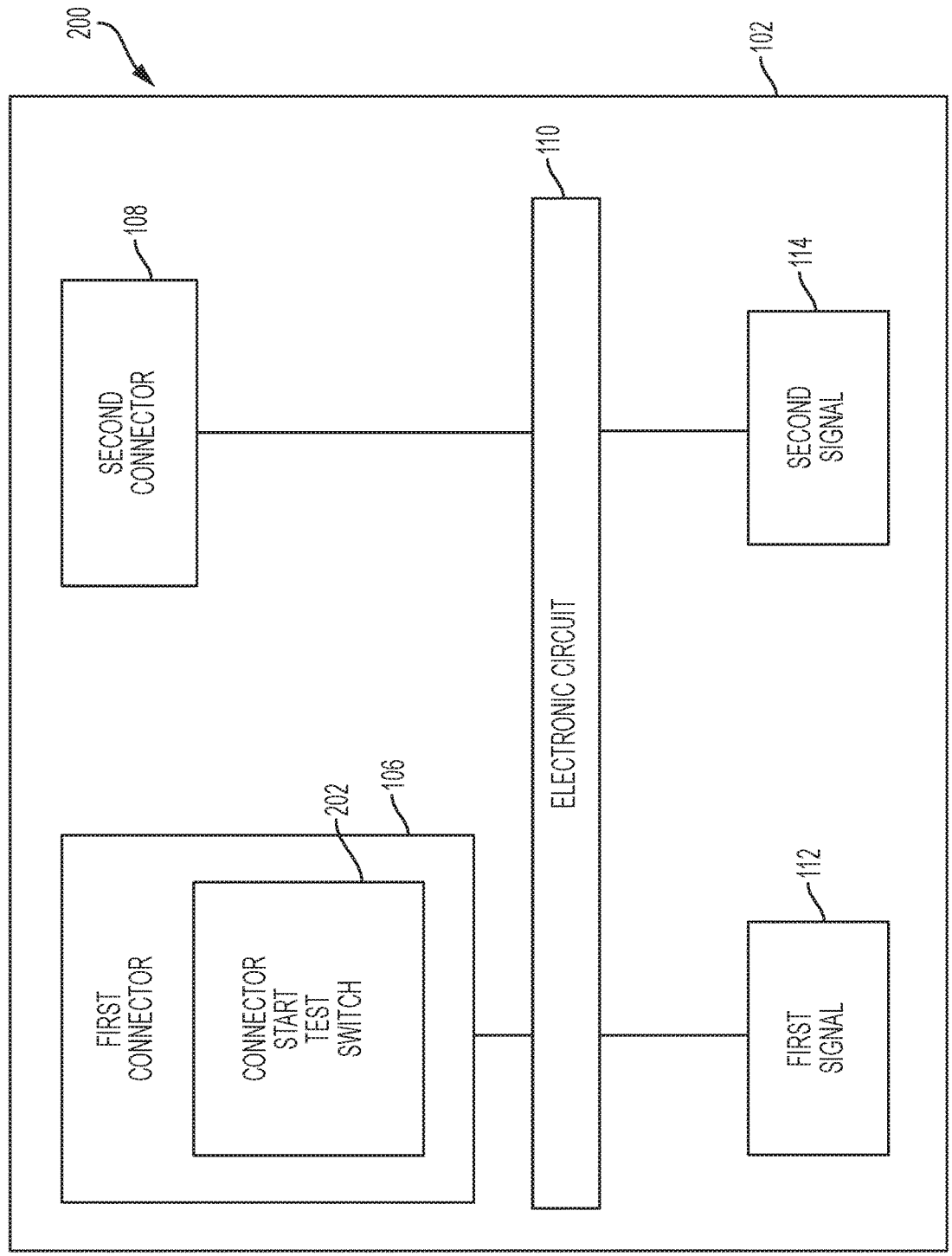
FIG. 2 shows a block diagram of an apparatus including the substrate, the first connector, the second connector, and the electronic circuit all shown in FIG. 1 and a connector start switch included in the first connector, according to some embodiments of the present disclosure.

FIG. 2 shows a block diagram of an apparatus 200 including the substrate 102, the first connector 106, the second connector 108, the electronic circuit 110, the first signal 112 and the second signal 114 all shown in FIG. 1 and a connector start switch 202 included in the first connector 106, according to some embodiments of the present disclosure. The connector start switch 202 is included in the first connector 106. In some embodiments, the connector start switch 202 is a pressure activated switch that is closed upon insertion of first end of the cable under test into the first connector 106.

Figure 3:
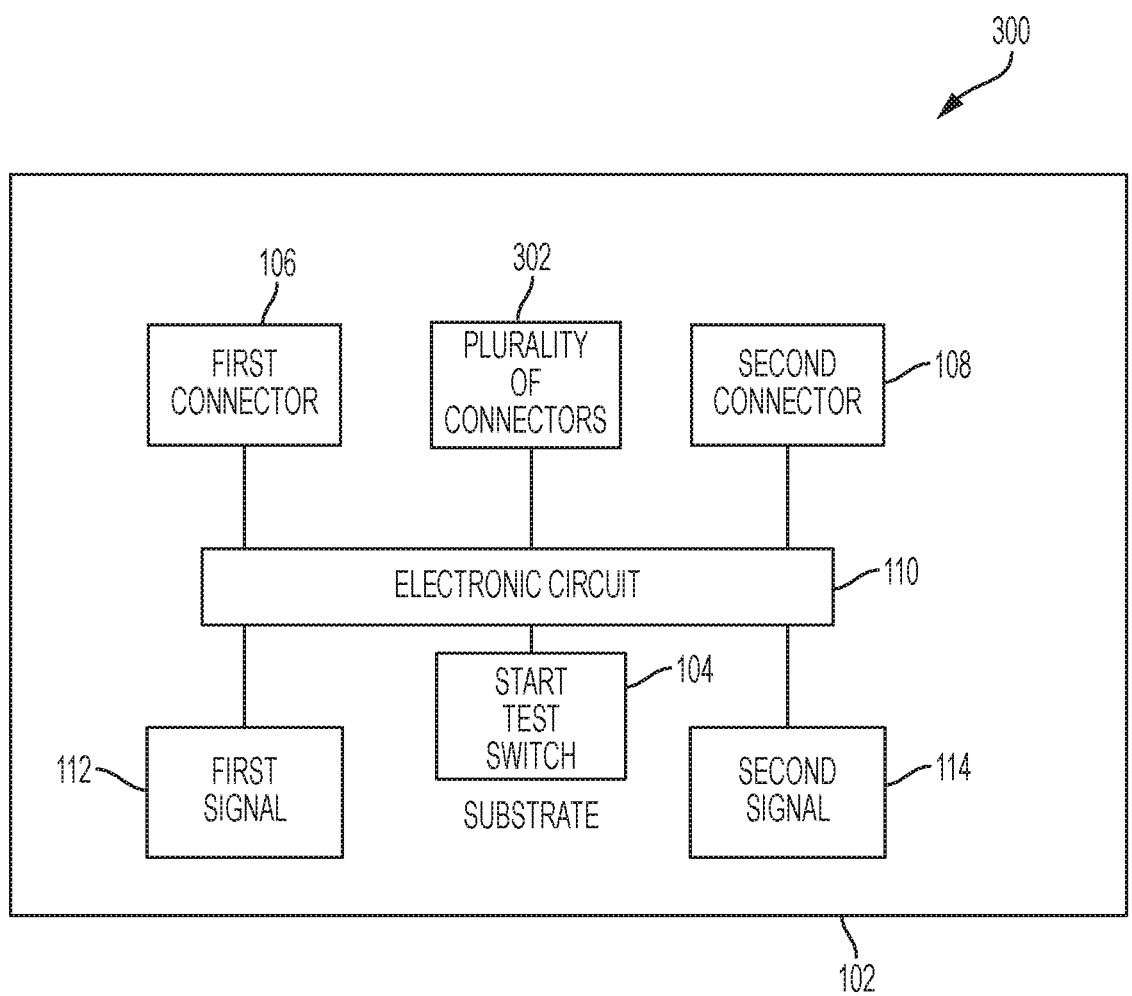
FIG. 3 shows a block diagram of an apparatus including the substrate, the start switch, the first connector, the second connector, and the electronic circuit all shown in FIG. 1 and a plurality of additional connectors, according to some embodiments of the present disclosure.

FIG. 3 shows a block diagram of an apparatus 300 including the substrate 102, the start switch 104, the first connector 106, the second connector 108, the electronic circuit 110, the first signal 112 and the second signal 114, all shown in FIG. 1 and a plurality of additional connectors 302. In some embodiments, the plurality of additional connectors 302 couples to two or more additional cables. The plurality of additional connectors 302 provide connectors for increasing the number and variety of cables that can be tested by the apparatus 300. For example, in some embodiments, two of the plurality of additional connectors 302 are designed to accommodate testing of an electrosurgical cable where the first end or the second end include a non-standard connector.

Figure 4:
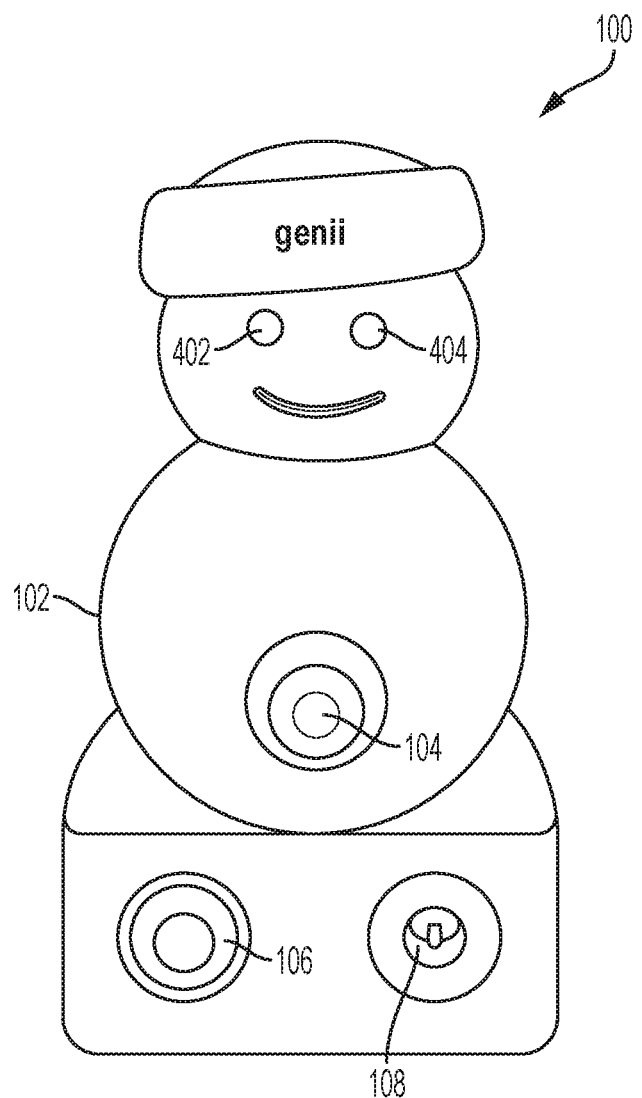
FIG. 4 shows a front perspective view of the apparatus illustrated in the block diagram of FIG. 1 including the substrate, the start switch, the first connector, the second connector, and further including a first light emitting diode and a second light emitting diode according to some embodiments of the present disclosure.

FIG. 4 shows a front perspective view of the apparatus 100 shown in the block diagram of FIG. 1 including the substrate 102, the start switch 104, the first connector 106, the second connector 108, and further including a first light emitting diode 402 and a second light emitting diode 404, according to some embodiments of the present disclosure. In some embodiments, the first light emitting diode 402 emits substantially green light and the second light emitting diode 404 emits substantially red light.

Figure 5:
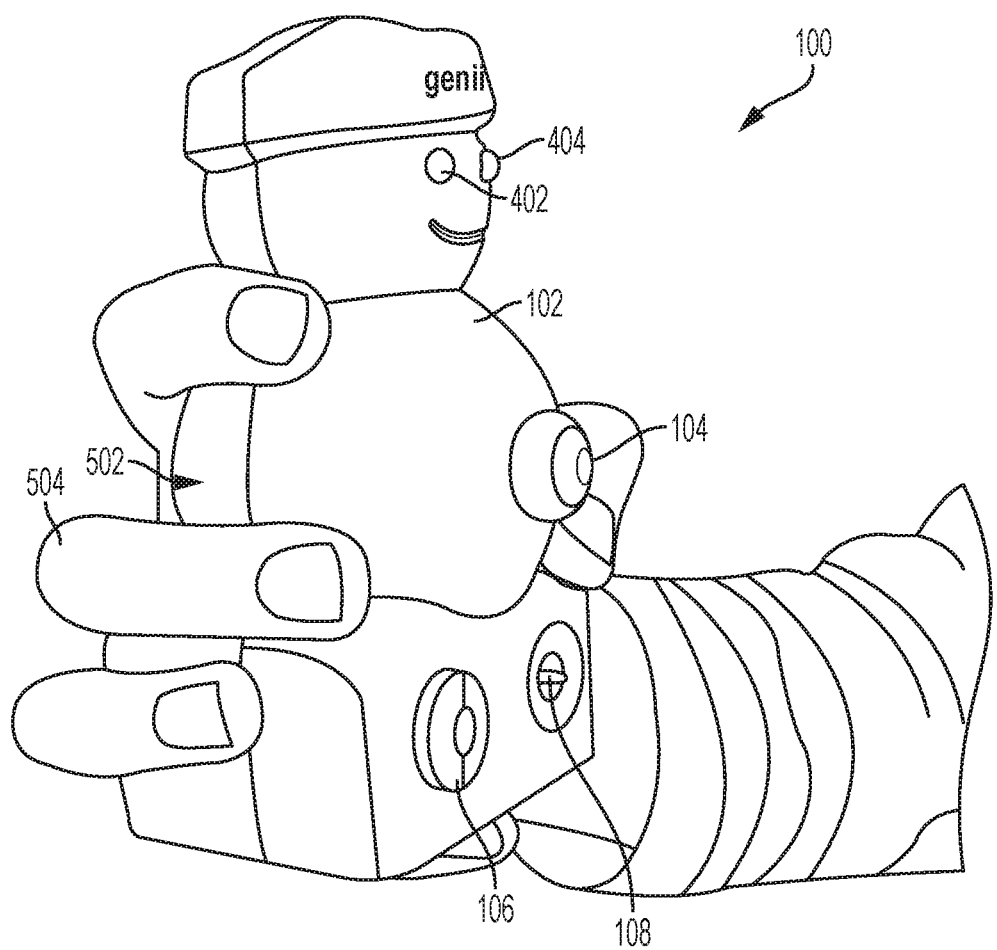
FIG. 5 shows a side perspective view of the apparatus shown in the block diagram of FIG. 1 including the substrate, the start switch, the first connector, and the second connector, and the substrate having a smoothly bending surface to fit into a human hand, according to some embodiments of the present disclosure.

FIG. 5 shows a side perspective view of the apparatus 100 shown in the block diagram of FIG. 1 including the substrate 102, the start switch 104, the first connector 106, and the second connector 108, and the substrate 102 having a smoothly bending surface 502 to fit into a human hand 504, according to some embodiments of the present disclosure. In some embodiments, the smoothly bending surface 502 includes a substantially spherical segment. In some embodiments, the substantially spherical segment has a radius of between about one inch and about six inches. The substrate 102 is not limited to enclosing a particular volume. In some embodiments, exemplary volumes for the substrate 102 can range from about 30 cubic inches to about 2500 cubic inches.

Figure 6:
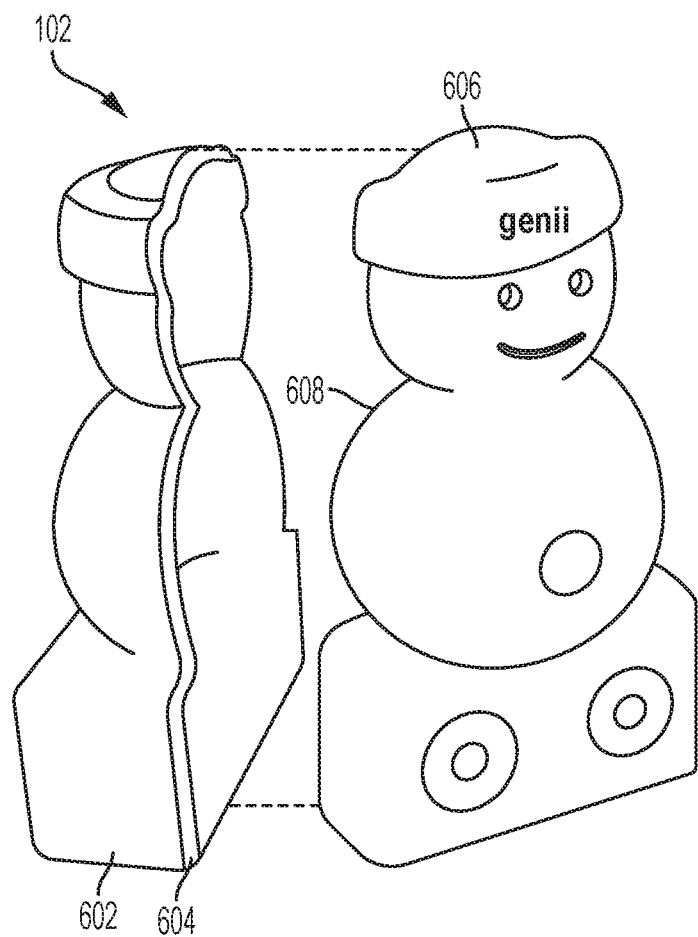
FIG. 6 shows an exploded view of the apparatus shown in FIG. 4, wherein the substrate comprises a first cross-section having a first cross-section edge and a second cross-section having a second cross-section edge, according to some embodiments of the present disclosure.

FIG. 6 shows an exploded view of the apparatus shown in FIG. 4, wherein the substrate 102 includes a first cross-section 602 having a first cross-section edge 604 and a second cross-section 606 having a second cross-section edge 608, according to some embodiments of the present disclosure. Coupling the first cross-section edge 604 to the second cross-section edge 608 forms an enclosure to hold the electronic circuit (shown in FIG. 1). Those skilled in the art will appreciate that the first cross-section 602 and the second cross-section 606 need not be formed as shown in FIG. 6, but rather can be defined in various ways to achieve different goals, such as ease of manufacture or assembly.

Figure 7:
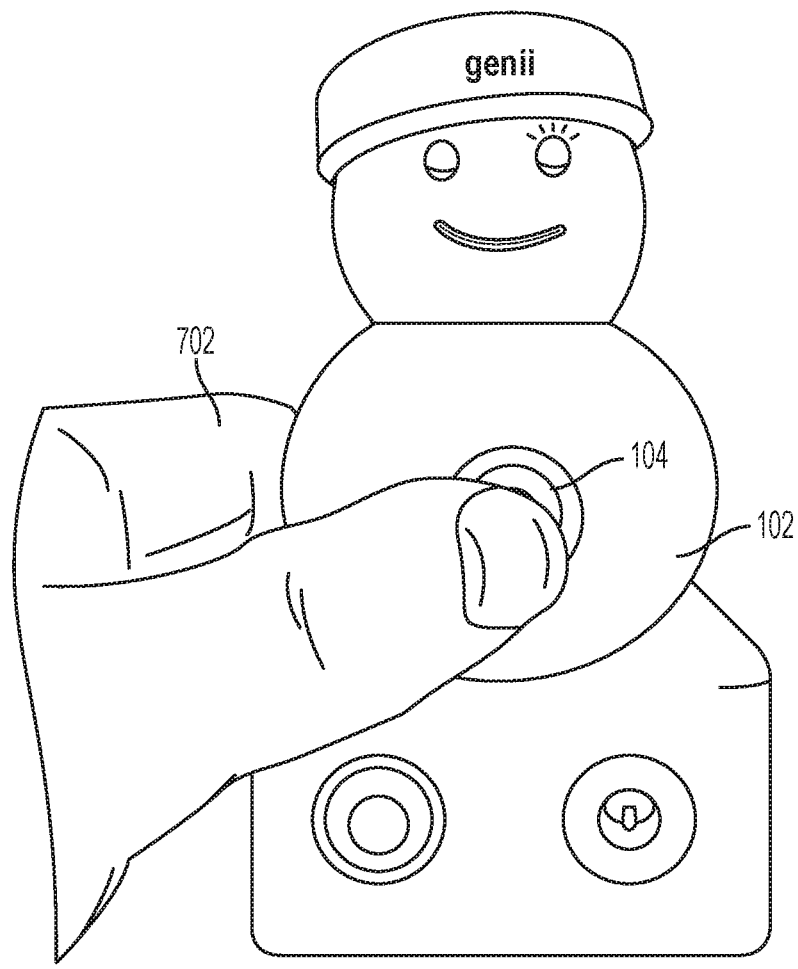
FIG. 7 shows a perspective view of the apparatus of FIG. 4 illustrating activation of the electronic circuit by a thumb depressing the touch activated switch, according to some embodiments of the present disclosure.

FIG. 7 shows a perspective view of the apparatus of FIG. 4 illustrating activation of the electronic circuit 110, shown in FIG. 1, by a thumb 702 depressing the start switch 104, according to some embodiments of the present disclosure. The volume of the substrate 102 can be designed to provide for ease of grasping the substrate 102 by a human hand and activating the switch 104.

Figure 8:
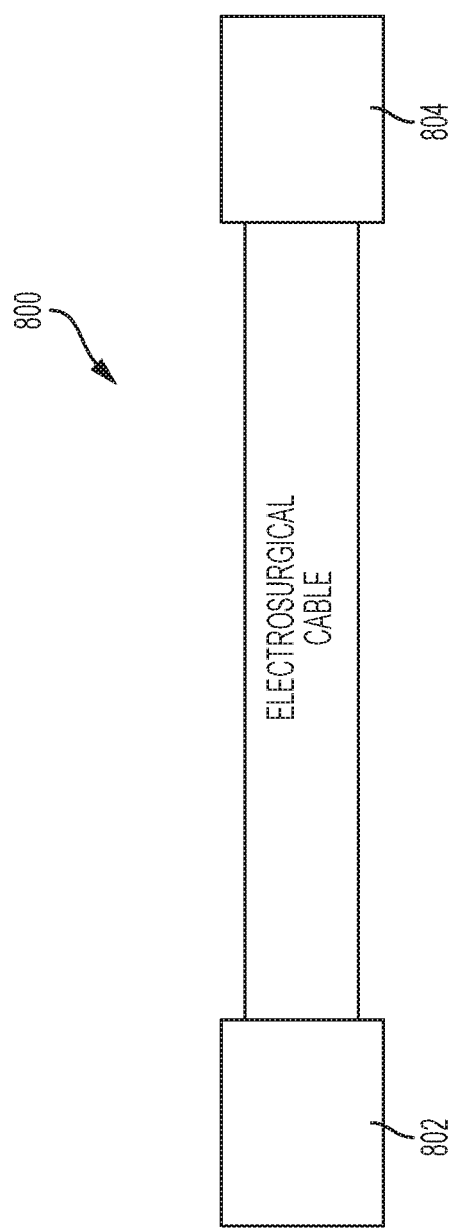
FIG. 8 shows an illustration of an electrosurgical cable including a first end and a second end suitable for testing by the apparatus of FIG. 4, according to some embodiments of the present disclosure.

FIG. 8 shows an illustration of an electrosurgical cable 800 including a first end 802 and a second end 804 suitable for testing by the apparatus of FIG. 4, according to some embodiments of the present disclosure.

Figure 9:
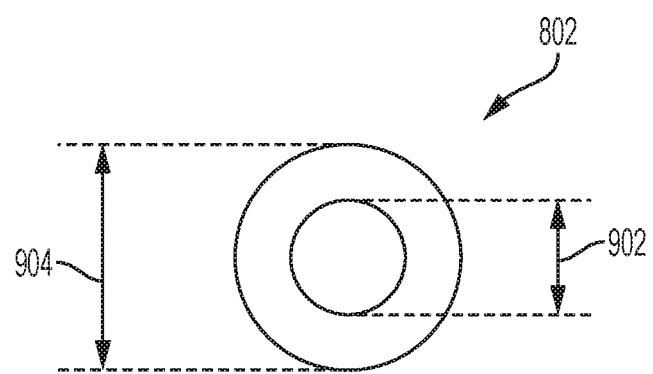
FIG. 9 shows a front view of the first end of the electrosurgical cable shown in FIG. 8 illustrating the first end having a first diameter or a second diameter different from the first diameter, according to some embodiments of the present disclosure.

FIG. 9 shows a front view of the first end 802 of the electrosurgical cable 800 shown in FIG. 8 illustrating the first end 802 having a first diameter 902 or a second diameter 904 different from the first diameter 902, according to some embodiments of the present disclosure.

Figure 10:
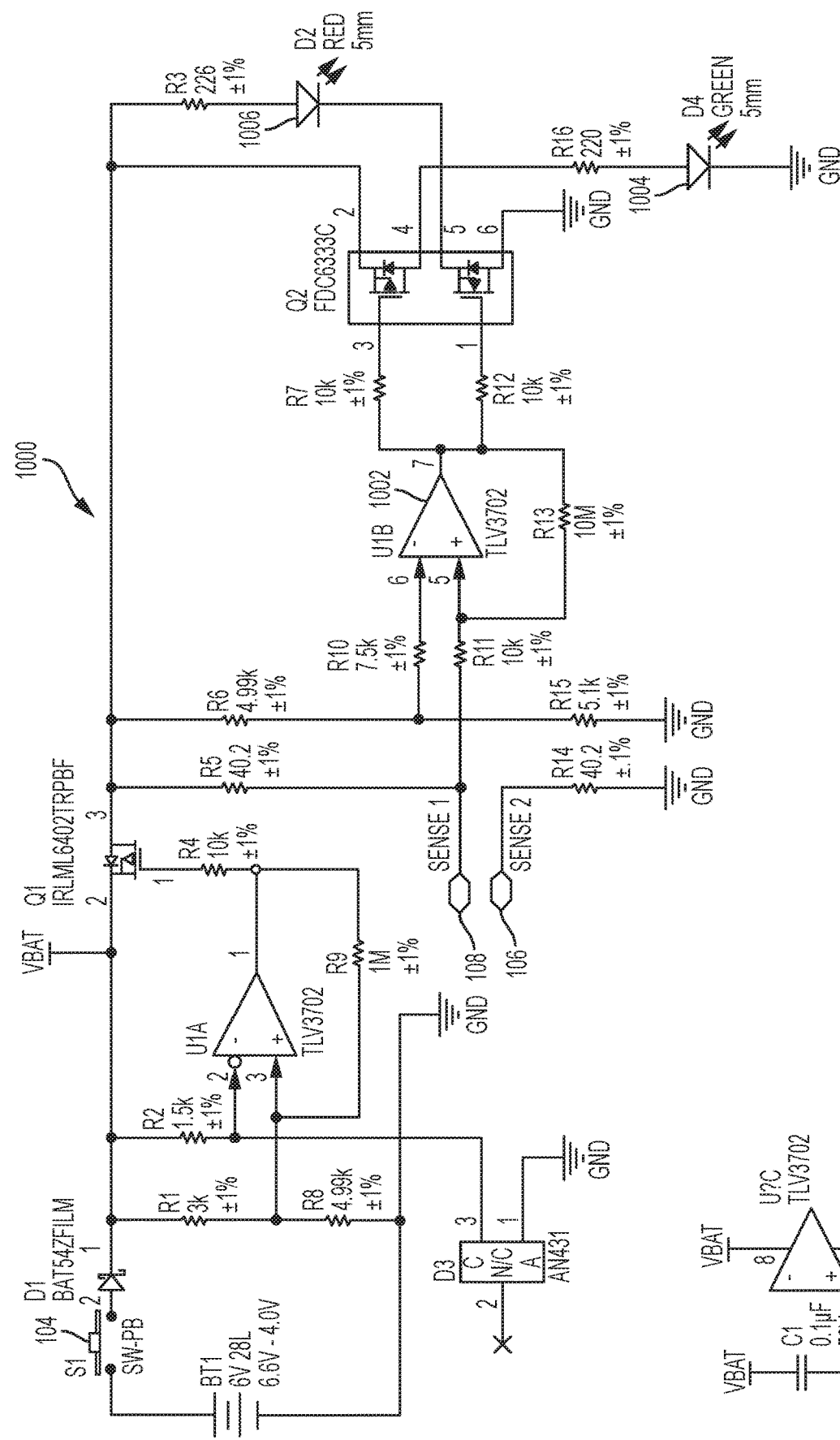
FIG. 10 shows a schematic diagram of the electronic circuit shown in the block diagram of FIG. 1, according to some embodiments of the present disclosure.

FIG. 10 shows a schematic diagram 1000 of the electronic circuit 110 shown in the block diagram of FIG. 1, according to some embodiments of the present disclosure. In operation, the first end 802 (shown in FIG. 8) of the cable 800 (shown in FIG. 8) under test is coupled to the first connector 106 and the second end 804 (shown in FIG. 8) of the cable under test is coupled to the second connector 108. The switch 104 is depressed and if the impedance of the cable under test is between a minimum impedance value and a maximum impedance value, then the comparator 1002 activates the green light emitting diode 1004. After the switch 104 is depressed, if the impedance exceeds the maximum impedance value, then the comparator 1002 activates the red light emitting diode 1006.

Figure 11:
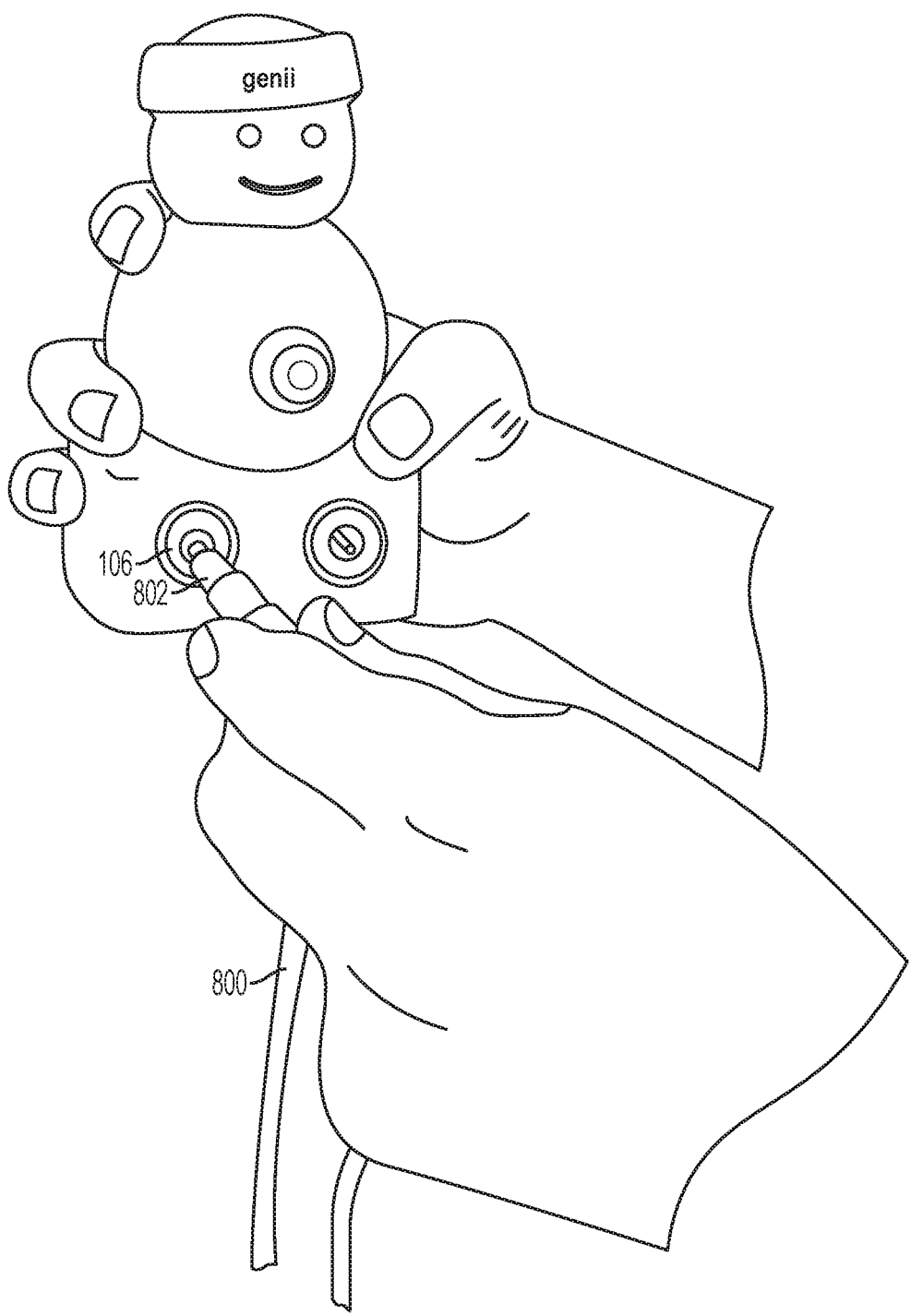
FIG. 11 shows a perspective view of the apparatus of FIG. 4 illustrating the first end of the cable inserted in the first connector, according to some embodiments of the present disclosure.
Figure 12:
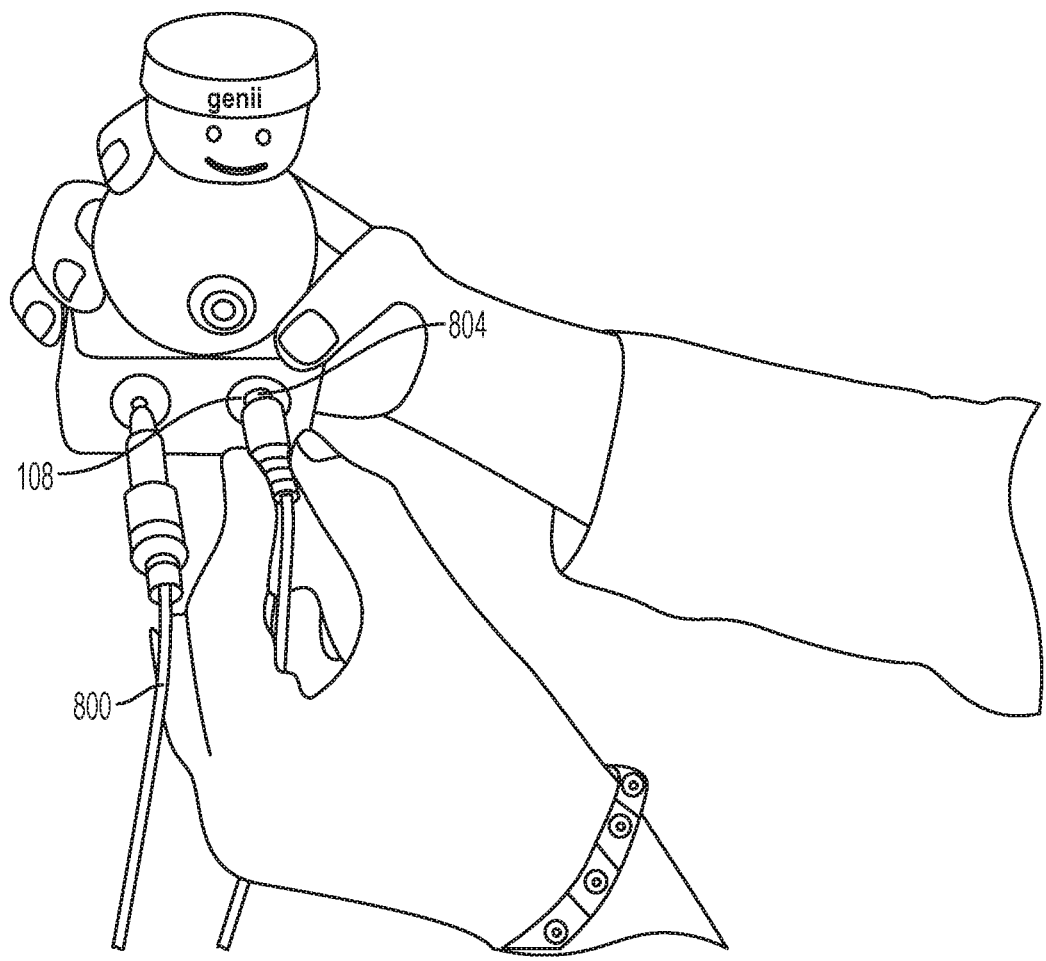
FIG. 12 shows a perspective view of the apparatus of FIG. 4 illustrating the second end of the cable inserted in the second connector, according to some embodiments of the present disclosure.

FIG. 11 and FIG. 12 show two steps for preparing the apparatus 100 to test a cable. FIG. 11 shows a perspective view of the apparatus of FIG. 4 illustrating the first end 802 of the electrosurgical cable 800 inserted in the first connector 106, according to some embodiments of the present disclosure. FIG. 12 shows a perspective view of the apparatus of FIG. 4 illustrating the second end 804 of the electrosurgical cable 800 inserted in the second connector 108, according to some embodiments of the present disclosure. After insertion of the first end 802 of the electrosurgical cable 800 in the first connector 106 and insertion of the second end 804 into the second connector 106, activation of the electronic circuit 110, as shown in FIG. 1, can be achieved, as shown in FIG. 7, by a thumb 702 depressing the start switch 104.

Figure 13:
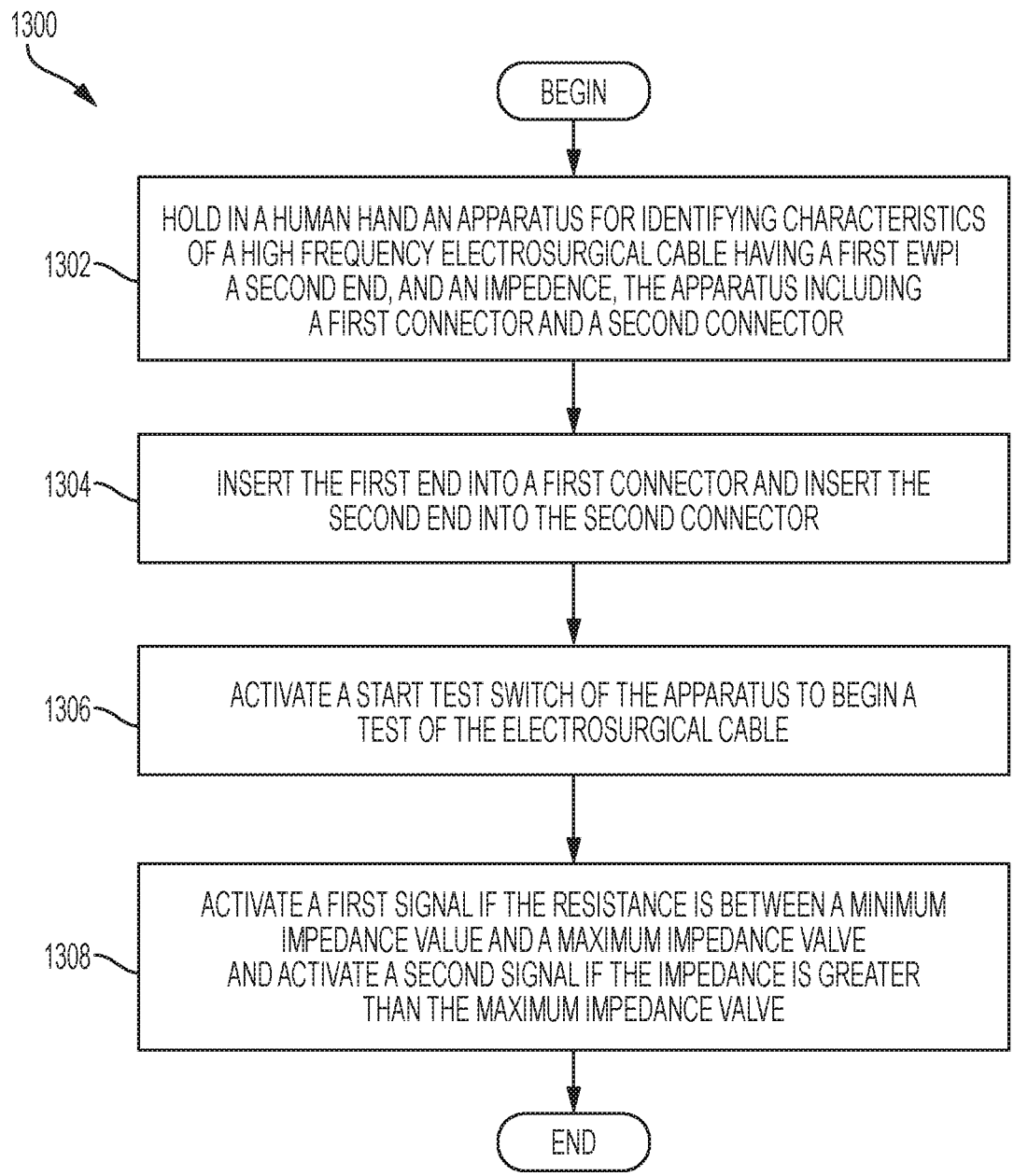
FIG. 13 shows a flow diagram of a method for using the apparatus shown in the block diagram of FIG. 1, according to some embodiments of the present disclosure.

FIG. 13 shows a flow diagram of a method 1300 for using the apparatus 100 shown in the block diagram of FIG. 1, according to some embodiments of the present disclosure. The method 1300 includes holding in a human hand an apparatus for identifying characteristics of a high frequency electrosurgical cable having a first end, a second end, and an impedance, the apparatus including a first connector and a second connector (block 1302), inserting the first end into a first connector and inserting the second end into the second connector (block 1304), activating a start test switch of the apparatus to begin a test of the electrosurgical cable (block 1306), and activating a first signal if the resistance is between a minimum impedance value and a maximum impedance value and activating a second signal if the impedance is greater than the maximum impedance value (block 1308).

In some embodiments, activating the start test switch included in the apparatus to begin the test of the high frequency electrosurgical cable comprises pressing a touch activated switch. In some embodiments, activating the start test switch included in the apparatus to begin the test of the high frequency electrosurgical cable comprises closing a switch when inserting the first end into the first connector. In some embodiments, activating the first signal if the resistance is between a minimum impedance value and a maximum impedance value and activating the second signal if the impedance of the electrosurgical cable is greater than the maximum impedance value comprises activating a first light emitting diode adapted to emit green light if the resistance is between the minimum impedance value and the maximum impedance value and activating a second light emitting diode adapted to emit red light if the resistance is greater than the maximum impedance value. In some embodiments, the method 1300 further includes displaying a first visual signal when the first signal is activated and displaying a second visual signal when the second signal is activated. In some embodiments, the method 1300 further includes generating a first audio signal when the first signal is activated and generating a second audio signal when the second signal is activated.

Reference throughout this specification to "an embodiment," "some embodiments," or "one embodiment." means that a particular feature, structure, material, or characteristic described in connection with the embodiment is included in at least one embodiment of the present disclosure. Thus, the appearances of the phrases such as "in some embodiments," "in one embodiment," or "in an embodiment," in various places throughout this specification are not necessarily referring to the same embodiment of the present disclosure. Furthermore, the particular features, structures, materials, or characteristics may be combined in any suitable manner in one or more embodiments.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. An apparatus comprising:
a substrate having a smoothly curving surface to fit into a human hand, the substrate including a start test switch, a first connector to couple to a first end of a cable, and a second connector to couple to a second end of the cable, the cable having an impedance; and
an electronic circuit coupled to the first connector and the second connector, the electronic circuit to provide a first signal when the first end of the cable is coupled to the first connector and the second end is coupled to the second connector, the start switch is activated, and the impedance is between a minimum impedance value and a maximum impedance value, the electronic circuit to provide a second signal when the first end of the cable is coupled to the first connector and the second end is coupled to the second connector, the start switch is activated, and the impedance is greater than the maximum impedance value, wherein the first connector couples to at least two high frequency electrosurgical cable connectors having different outside diameters.

2. The apparatus of claim 1, wherein the substrate comprises a first cross-section having a first cross-section edge and a second cross-section having a second cross-section edge wherein coupling the first cross-section edge to the second cross-section edge forms an enclosure to hold the electronic circuit.

3. The apparatus of claim 1, wherein the smoothly curving surface comprises a matte finish.

4. The apparatus of claim 1, wherein the spherical segment has a radius of between about one inch and about six inches.

5. The apparatus of claim 1, wherein the cable is a high frequency surgical cable.

6. The apparatus of claim 1, wherein the first connector is a high frequency electrosurgical cable connector.

7. The apparatus of claim 1, wherein the start test switch device comprises a touch activated switch.

8. The apparatus of claim 1, wherein the first signal is detectable by a human visual system.

9. The apparatus of claim 1, wherein the first signal is detectable by a human auditory system.

10. The apparatus of claim 1, wherein the first signal is provided by a light emitting diode adapted to emit a substantially green signal and the second signal is provided by a light emitting diode adapted to emit a substantially red signal.

11. The apparatus of claim 1, wherein the substrate has a volume of between about 30 cubic inches and about 2500 cubic inches.

12. An apparatus comprising:
    a substrate having a smoothly curving surface to fit into a human hand, the substrate including a start test switch, a first connector to couple to a first end of a cable, and a second connector to couple to a second end of the cable, the cable having an impedance; and
    an electronic circuit coupled to the first connector and the second connector, the electronic circuit to provide a first signal when the first end of the cable is coupled to the first connector and the second end is coupled to the second connector, the start switch is activated, and the impedance is between a minimum impedance value and a maximum impedance value, the electronic circuit to provide a second signal when the first end of the cable is coupled to the first connector and the second end is coupled to the second connector, the start switch is activated, and the impedance is greater than the maximum impedance value, wherein the minimum impedance value is about zero ohms and the maximum impedance value is about 1.1 ohms.

13. An apparatus comprising:
    a substrate having a smoothly curving surface to fit into a human hand, the substrate including a start test switch, a first connector to couple to a first end of a cable, and a second connector to couple to a second end of the cable, the cable having an impedance; and
    an electronic circuit coupled to the first connector and the second connector, the electronic circuit to provide a first signal when the first end of the cable is coupled to the first connector and the second end is coupled to the second connector, the start switch is activated, and the impedance is between a minimum impedance value and a maximum impedance value, the electronic circuit to provide a second signal when the first end of the cable is coupled to the first connector and the second end is coupled to the second connector, the start switch is activated, and the impedance is greater than the maximum impedance value, wherein the minimum impedance value is about 0.01 ohms and the maximum impedance value is about eight ohms.

* * * * *